United States Patent [19]

Hata et al.

[11] Patent Number: 4,579,734
[45] Date of Patent: Apr. 1, 1986

[54] NOVEL LACTOBACILLUS AND USES THEREFOR

[75] Inventors: Kosei Hata; Toshiyuki Maruoka, both of Osaka, Japan

[73] Assignee: Seikenkai Foundational Juridical Person, Japan

[21] Appl. No.: 511,805

[22] Filed: Jul. 7, 1983

[30] Foreign Application Priority Data

Jul. 12, 1982 [JP] Japan .................. 57-119890

[51] Int. Cl.$^4$ .................. A01N 63/00; A23C 9/12; C12R 1/225
[52] U.S. Cl. .................. 424/93; 426/8; 426/56; 426/61; 426/71; 426/335; 435/853; 435/253
[58] Field of Search .............. 435/853, 253; 426/52, 426/56, 335, 523, 8, 61, 42, 43, 71, 34, 7; 424/93

[56] References Cited

U.S. PATENT DOCUMENTS

| | | | |
|---|---|---|---|
| 3,193,391 | 7/1965 | Jansen et al. | 426/56 |
| 3,899,594 | 8/1975 | Nickerson et al. | 426/52 |
| 3,900,572 | 8/1975 | Peer | 426/52 |
| 4,160,038 | 7/1979 | Groben et al. | 426/56 |

FOREIGN PATENT DOCUMENTS

| | | | |
|---|---|---|---|
| 1073136 | 6/1976 | Japan . | |
| 8014628 | 5/1978 | Japan . | |
| 8020432 | 6/1978 | Japan | 426/56 |
| 5048386 | 4/1980 | Japan . | |
| 01644742 | 12/1981 | Japan | 426/52 |

*Primary Examiner*—Sam Rosen
*Assistant Examiner*—William J. Herald
*Attorney, Agent, or Firm*—Sughrue, Mion, Zinn, Macpeak, and Seas

[57] ABSTRACT

A novel *Lactobacillus clearans*, *Lactobacillus sulfurica* and *Lactobacillus nitrosus*:

which can decrease both $Na_2S.9H_2O$ and/or $NH_3$ when inoculated and cultured on:

a medium comprising 5 g of meat extract, 5 g of peptone, 0.5 g of $Na_2S.9H_2O$, 5 g of glucose, 1 g of $CaCO_3$, 0.5 ml of $NH_3$ (as 100% ammonia) and 1 liter of water (pH, neutral);

which shows no growth acceleration action even when said bacteria is cultured on a medium comprising a Stephenson-Wetham medium (hereafter merely referred to as (S-W); $KH_2PO_4$ 1 g, $MgSO_4.7H_2O$ 0.7 g, NaCl 1 g, $(NH_4)_2HPO_4$ 4 g; $FeSO_4.7H_2O$ 0.03 g, glucose 5 g)+vitamins (A: 900 IU, $B_1$: 1 mg, $B_2$: 1 mg, $B_6$: 1 mg, $B_{12}$: 5 gamma nicotinamide: 1.6 mg, calcium pantothenate: 8 mg, C: 64 mg, $D_2$: 120 IU)+casamino acid 1 g and 0.5 g of $Na_2S.9H_2O$ and/or 0.5 ml (100% conversion) of $NH_3$ are incorporated at the logarithmic growth phase; and;

which has the following characteristics:

gram-positive, rod, non-motile, catalase-negative, no reduction of nitrates, no decomposition of gelatin, no formation of indole or hydrogen sulfide, high ability of forming lactic acid from glucose and lactose, and growth being accelerated by the addition of acetic acid.

12 Claims, 2 Drawing Figures

NOVEL LACTOBACILLUS AND USES THEREFOR

BACKGROUND OF THE INVENTION

1. Field of the Invention

The present invention relates to a novel type Lactobacillus bacteria and, more particularly to novel *Lactobacillus clearnas, Lactobacillus sulfurica* and *Lactobacillus nitrosus* which are characterized by not having its growth accelerated by $Na_2S.9H_2O$ and/or $NH_3$, but instead reduces those two materials under specified conditions.

2. Development of the Invention

Conventionally known Lactobacilli are gram-positive, anaerobic or slightly aerobic, asporogenic rods and, depending upon the strain, Lactobacilli are in a cocci or bacilli form, curved form, coryneform, filiform, etc. They are non-motile, catalase-negative and do not reduce nitrates. Further, they do not decompose gelatin and do not produce indole or hydrogen sulfide. Some strains exhibit staining at their terminals. They have extremely weak proteolytic and lipolytic activity, grow well under an anaerobic or slightly aerobic condition rather than under an aerobic condition, are strongly saccharolytic, acid resistant, produce lactic acid in a yield of more than 50% by the fermentation of glucose and their growth is accelerated by the addition of acetic acid to the culture medium. They exhibit no pathogenicity to animals and plants.

It is also known that nutritional requirements of these bacteria are high, and they cannot grow unless a culture medium having a very high nutritional composition is used. That is, amino acids, peptides, nucleic acid derivatives, vitamins, salts, fatty acids or fatty acid esters and fermentable carbohydrates are required.

Classification of such Lactobacilli as to "species" has been heretofore evaluated by (a) saccharolysis, (b) gas production, (c) optical rotation, (d) growth temperature range and (e) growth pH range (*Bergeys Manual of Determinative Bacteriology*, 8th Edition, pages 576 to 578).

Among the aforesaid classification related items for evaluation, however, (e) growth pH range is variable to a certain extent, depending upon adaptability of the bacteria; and (c) optical rotation is an issue relating to commercial products rather than relating to in vivo characteristics. If one considers characterization items for evaluation relating to the intestine, oral cavity and vagina habitats of the bacteria, (a) saccharolysis is relevant only in relation to feed decomposition by the bacteria. Therefore, the relation of bacteria to its habitat and further to its function therein are not shown with a high correlation; the aforesaid bacterial classification is very distantly related to a classification based on the activities of the bacteria in a habitat filled with putrid substances, under an environment to prevent invasion of external enemies and where the order of $5 \times 10^8$ cells/g survive. This inconsistency is now a cause for markedly restricting studies per se on Lactobacilli. This is because classification is a basis for developing a study protocol. In actuality, it has been desired that the conditions of the natural habitat of Lactobacilli be fully taken into account and bacterial classification be evaluated by mode of activity therein as early as possible.

For example, food orally administered is decomposed in the intestine and gradually absorbed in the living body on the one hand, and on the other hand, excreted via the course of putrefaction. The formation of putrid material is greatly dependent on enteric putrid bacteria. The putrid substance is also absorbed through blood vessels surrounding the intestinal tube and directly threatens the intestine and blood vessels in that area. For example, it has been reported that for repair of an intestinal tube injured due to ammonia produced in the intestinal tube, 4% of the energy in food is consumed (experiment using chickens).

It has been clarified by the present inventors that in directly correlating bacterial properties to materials present in the intestine, bacteria having a function of reducing enteric malignant materials such as $H_2S$ or $NH_3$ are considerably present in the *Lactobacilli flora*. This is an extremely important matter because effectiveness of the Lactobacilli has been actually proven on a material level, apart from a viewpoint of epidemiological or statistical studies. Further, speaking from a bacteriological standpoint, this discovery is influential in developing a fundamental solution to the inconsistency in conventional classification, strongly suggesting that criteria for classification be set forth quite different from conventional classification items. The two materials described above ($NH_3$ and $N_2S$) are both not only representative of noxious materials in the intestine, but together with butyric acid are also alternatives for the various compounds containing sulfur atoms, nitrogen atoms and carbon atoms (Hereinfter referred to as S, N and C-compounds respectively) found in the intestine, as described in our Japanese Pat. Nos. 938,917 and 936,213.

As has been described before in detail, studies on the relationship between classification evaluation items of Lactobacilli and their habitat were insufficient in the past, with poor correlation as described above. As a new concept, however, introduction of $Na_2S.9H_2O$ and $NH_3$ as items of evaluation for classification of Lactobacilli has clarified that there is an extremely high correlation between bacterial properties and nomenclature of bacteria well known in the art, and the aforesaid two materials. That is, Lactobacilli can be classified into one of the groups below, based on their behavior to these materials.

(a) Group of bacteria which is found to be incapable of residing in the intestine—bacteria which are sensitive to $Na_2S.9H_2O$ and $NH_3$ and have no ability to reduce the levels of both of those materials.

(b) Group of bacteria such as acidophilus which have been said to be resident in the intestine—which are insensitive to $Na_2S.9H_2O$ and $NH_3$ but have no ability to reduce the levels of both of those materials.

The bacteria belonging to (a) and (b) described above are strains all isolated by senior researchers which are classified in points different from behavior to $Na_2S.9H_2O$ and $NH_3$. Separately, the present inventors have already clarified in Japanese Pat. Nos. 938,917 and 936,213 and Japanese Patent Application No. 134773/74 that there are present Lactobacilli which are poor in nutritional requirements and the growth of which is accelerated not only by lower fatty acids such as acetic acid but also by $Na_2S.9H_2O$ and $NH_3$, in a medium having poor nutritional composition.

SUMMARY OF THE INVENTION

Now the present inventors have found Lactobacilli having properties previously quite unknown. This bacteria can be found from auxotrophic bacteria which can grow in a (Stephenson-Wetham medium+vitamins+- casamino acid) medium in which commercially available Lactobacilli well known in the art, to poor auxotrophic bacteria, as disclosed in Japanese Pat. Nos. 938,917 and 936,213 and Japanese Patent Application No. 134773/74, grow. In addition, the properties of the novel bacteria are all consistent with the definitions of Lactobacilli observed in conventional Lactobacilli described above.

In addition, however, these bacteria have properties that no growth acceleration is exhibited either in the presence of either of $Na_2S.9H_2O$ and $NH_3$ or in the presence of both, but these bacterial have an activity of reducing either of $Na_2S.9H_2O$ and $NH_3$ or both materials described above under growth survival environmental conditions. Further, it has been confirmed that notwithstanding most are not as poor in auxotrophy as conventionally well known Lactobacilli, their capability of digesting noxious materials is inherent to the bacteria per se since variation of titer due to transfer is extremely small and stable.

Accordingly, the present inventors have named the novel bacteria in accordance with the present invention to be *Lactobacillus clearans* for bacteria reducing $Na_2S.9H_2O$ and $NH_3$, *Lactobacillus sulfurica* for bacteria reducing $Na_2S.9H_2O$ and *Lactobacillus nitrosus* for bacteria reducing $NH_3$ as species *nova*.

A Russian researcher, Mechinikov (1845-1916), proposed a toxicity theory, alleging that a major cause for the aging of the human body is due to noxious materials produced by putrefactive fermentation in the intestine and, as a countermeasure, he proposed that it is helpful to drink yogurt to prevent aging. Now the present inventors have come to find a group of bacteria which can clearly reduce noxious materials and it can be said that a food containing the bacteria of the present invention would follow Mechinikov's theory. In addition, it should be noted that the ability of the novel group of bacteria in accordance with the present invention to reduce a series of noxious materials in extremely mild in action and has little impact on the living body, which maintains a certain balance with the noxious materials, as is evident from experimental data shown in this specification.

Thus, the present invention relates to a novel *Lactobacillus clearans, Lactobacillus sulfurica* and *Lactobacillus nitrosus*:

which can decrease both $Na_2S.9H_2O$ and/or $NH_3$ when inoculated and cultured on:

a medium comprising 5 g of meat extract, 5 g of peptone, 0.5 g of $Na_2S.9H_2O$, 5 g of glucose, 1 g of $CaCO_3$, 0.5 ml of $NH_3$ (as 100% ammonia) and 1 liter of water (pH, neutral);

which shows no growth acceleration action even when said bacteria is cultured on a medium comprising a Stephenson-Wetham medium (hereafter merely referred to as (S-W); $KH_2PO_4$ 1 g, $MgSO_4.7H_2O$ 0.7 g, NaCl 1 g, $(NH_4)_2 HPO_4$ 4 g; $FeSO_4.7H_2O$ 0.03 g, glucose 5 g)+vitamins (A: 900 IU, $B_1$: 1 mg, $B_2$: 1 mg, $B_6$: 1 mg, $B_{12}$: 5 gamma, nicotinamide: 1.6 mg, calcium pantothenate: 8 mg, C: 64 mg, $D_2$: 120 IU)+ casamino acid 1 g and where 0.5 g of $Na_2S.9H_2O$ and/or 0.5 ml (100% conversion) of $NH_3$ are incorporated at the logarithmic growth phase; and;

which has the following characteristics;

gram-positive, rod, non-motile, catalase-negative, no reduction of nitrates, no decomposition of gelatin, no formation of indole or hydrogen sulfide, high ability of forming lactic acid from glucose and lactose, and growth being accelerated by the addition of acetic acid.

The present inventors have disclosed bacteria, the growth of which is accelerated due to $Na_2S.9H_2O$ and $NH_3$ in Japanese Pat. Nos. 938,917 and 936,213 and Japanese Patent Application No. 134773/74. However, the inventors made extensive investigations on utilization of those bacteria and maintenance of a potent titer thereof, rather than investigations in the historical sense. Since their early work approximately 10 years has passed, but the inventors have not noted any article or report relating hereto, nor speaking of utilization of the industrially highly significant bacterial group shown in the present invention.

In obtaining the bacteria of the present invention, isolation technique is of importance. It is possible to isolate bacteria belonging to the species (*L. clearans, L. sulfurica* and *L. nitrosus*) of the present invention from many strains over a short period of time.

It is thus notable that according to the present invention, bacteria having a function of reducing noxious materials in the intestine in a considerably high rate can easily be isolated and obtained, notwithstanding that the bacteria is otherwise characterized the same as Lactobacillus well known in the art.

It is also notable that the bacteria of the present invention is isolated from the bacteria, among Lactobacilli, which reside in the intestine, so that the bacteria of this invention has already been adapted by nature to cohabit with other enteric bacteria; accordingly, the bacteria of the present invention hardly causes disturbance to the bacterial flora of the intestine, when administered to the human body.

PREFERRED EMBODIMENTS OF THE INVENTION

Figure 1:
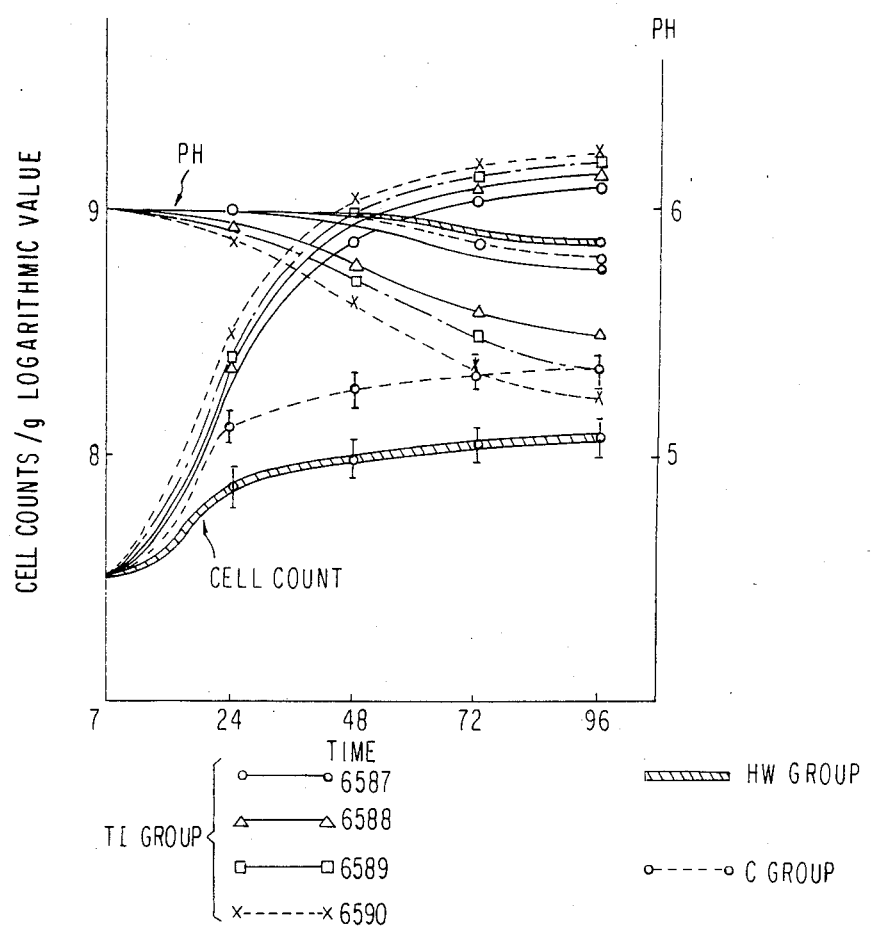
FIG. 1 is a graph showing growth curves and change in pH of a medium when a bacteria in accordance with the present invention and a bacteria for comparison were cultured in cream, respectively.

Experimental data relating to 6 strains among the novel strains in accordance with the present invention is given below.

Four kinds of strains in accordance with the present invention, which were deposited in Institute for Fermentation, Osaka, under the accession numbers IFO 14253, 14254, 14255, 14256, 14257 and 14258. were inoculated in a medium consisting of 5 g of meat extract, 5 g of peptone, 0.5 g of $Na_2S.9H_2O$, 1 g of glucose, 1 g of $CaCO_3$ and 1 liter of water (pH, neutral). After culturing at 37° C., reduction of $Na_2S.9H_2O$ was examined 24, 48 and 72 hours later, respectively.

The results are shown in Table 1.

TABLE 1

| Item Examined IFO No. | Decreased Amount of $Na_2S.9H_2O$ (mg) Culturing Time | | |
|---|---|---|---|
| | 24 hrs. | 28 hrs. | 72 hrs. |
| 14253 | 100 | 200 | 250 |
| 14254 | 250 | 375 | 400 |
| 14255 | 100 | 200 | 250 |
| 14256 | 100 | 200 | 250 |
| 14257 | 0 | 0 | 0 |

TABLE 1-continued

| Item Examined | Decreased Amount of Na$_2$S.9H$_2$O (mg) Culturing Time | | |
|---|---|---|---|
| IFO No. | 24 hrs. | 28 hrs. | 72 hrs. |
| 14258 | 0 | 0 | 0 |

As is evident from the results shown in Table 1, it is well understood that even such a noxious compound, e.g., Na$_2$S.9H$_2$O decreases at a surprising rate except for strains IFO 14257 and 14258. The results shown in the table above are those obtained when 500 mg (0.5 g) of Na$_2$S.9H$_2$O was incorporated into the medium; but even when 1000 mg and 1300 mg were incorporated, the decreased amount of Na$_2$S.9H$_2$O was almost the same.

The method for measuring the decreased amount of Na$_2$S.9H$_2$O comprises dropwise adding a 0.1% lead acetate solution, with the dropwise addition amount being suitably 1 vol.% of the medium, thoroughly shaking immediately after completion of the dropwise adding, and measuring color tone (black-grey-white) of the residual Na$_2$S with a colorimeter or an absorptiometric method using Methylene Blue [L. Gustafsion, Talanta, 4,227 (1960)].

Next, the same 8 strains as in Table 1 were inoculated on a medium consisting of 5 g of meat extract, 5 g of peptone, 1 g of glucose, 1 g of CaCO$_3$, 0.5 ml of NH$_3$ (calculated as 100%) and 1 liter of water (pH, neutral) followed by culturing at 37° C. for 24, 48 and 72 hours, respectively. It was examined to what extent NH$_3$ content was decreased.

The results are shown in the following Table 2.

TABLE 2-(1)

| Item Examined | Decreased Amount of NH$_3$ (100% conversion) (ml) Culturing Time | | |
|---|---|---|---|
| IFO No. | 24 hrs. | 48 hrs. | 72 hrs. |
| 14253 | 100 | 200 | 250 |
| 14254 | 200 | 350 | 375 |
| 14255 | 0 | 0 | 0 |
| 14256 | 0 | 0 | 0 |
| 14257 | 100 | 200 | 250 |
| 14258 | 100 | 200 | 250 |

As is understood from the results shown in Table 2, bacteria causing a marked decrease of NH$_3$ were present, except for strains IFO 14255 and 14256. In this experiment, 0.5 ml of NH$_3$ was incorporated in the medium but even when the amount changed to 1.3 ml, the decreased amount is almost the same as those shown in the above table.

The method for measuring a decreased amount of NH$_3$ comprises dropwise adding a 10% solution of commercially available Nessler's reagent (mercuric iodate—2 W/V%) with the dropwise addition amount being 1% by volume of the medium, thoroughly shaking immediately after completion of the dropwise addition and measuring orange tone (orange-yellow) of the residue with a colorimeter or an absorptiometer using indophenol method.

The 6 strains as in Table 2-(2) were inoculated on a medium consisting of 5 g of meat extract, 5 g of peptone, 1 g of glucose, 1 g of CaCO$_3$, 0.5 ml of NH$_3$ (calculated as 100%), 0.5 g of Na$_2$S.9H$_2$O and 1 liter of water (pH, neutral). After culturing at 37° C., reductions of Na$_2$S.9H$_2$O and NH$_3$ were examined 24, 48 and 72 hours later, respectively. The results are shown in Table 2-(2).

TABLE 2-(2)

| | Na$_2$S.9H$_2$O + NH$_3$ | | | | | |
|---|---|---|---|---|---|---|
| | Decreased Amount of Na$_2$S.9H$_2$O (mg) | | | Decreased Amount of NH$_3$ (100% conversion) (ml) | | |
| | 24 hrs. | 48 hrs. | 72 hrs. | 24 hrs. | 48 hrs. | 72 hrs. |
| 14253 | 100 | 200 | 250 | 100 | 200 | 250 |
| 14254 | 250 | 350 | 400 | 200 | 300 | 350 |
| 14255 | 100 | 200 | 250 | 0 | 0 | 0 |
| 14256 | 100 | 200 | 250 | 0 | 0 | 0 |
| 14257 | 0 | 0 | 0 | 100 | 200 | 250 |
| 14258 | 0 | 0 | 0 | 100 | 200 | 250 |

Isolation of the bacteria group in accordance with the present invention is carried out as follows:

(1) Composition (a) containing 5 g of meat extract, 5 g of peptone, 0.3 g of Na$_2$S.9H$_2$O and/or 0.5 ml of NH$_3$, 3 g of sodium butyrate, 5 g of glucose and 3 g of CaCO$_3$ and composition (b) containing 5 g of peptone, 0.3 g of Na$_2$S.9H$_2$O and/or 0.5 ml of NH$_3$, 5 g of sodium butyrate, 10 g of glucose and 3 g of CaCO$_3$, in 1 liter of a medium are prepared. The pH is modified to neutral and diluted feces of living creatures, such as pig, horse, cow, mankind, chicken, etc., is coated on the medium followed by anaerobic culturing at 37° C.

(2) Among appeared colonies, colonies having a transparent margin are fished.

(3) The colonies are spread over an LBS medium* followed by culturing at 37° C. for 2 days.

* 10 g of trypticase, 5 g of yeast extract, 10 g of meat extract, 6 g of KH$_2$PO$_4$, 2 g of diammonium citrate, 20 g of glucose, 1 g of Tween 80, 40 g of sodium acetate, 15 ml of Solution B and 3.7 ml of glacial acetic acid (99.5%), pH adjusted, sterilization is not necessary; Solution B: 0.5 g of FeSO$_4$.7H$_2$O; 2.47 g of MnSO$_4$.nH$_2$O, 0.5 g of NaCL, 10 g of MgSO$_4$.7H$_2$O and 250 ml of water.

(4) Grown colonies are fished and stab culture is carried out on a butt medium consisting of 10 g of meat extract, 10 g of peptone, 2 g of NaCl, 10 g of glucose, 5 g of lime and 10 g of agar to collect gas-non-producing bacteria.

(5) Various tests are performed to see if the properties of the bacteria are consistent with those of Lactobacilli and it is confirmed that the bacteria is classified as Lactobacilli from a taxonomy standpoint.

(6) Hemolytic test is carried out to collect non-hemolytic bacteria.

(7) It is examined whether or not Na$_2$S.9H$_2$O and/or NH$_3$ are descreased (the medium to be used and the measurement method have been described hereinbefore).

(8) Test for nutritional requirements of the bacteria is carried out.

(9) Classification is made, taking into account (7) and (8) above further considering saccharolytic capability in combination therewith.

(10) Mu ($\mu$*) is measured in various media from rich to poor nutrition.
* If the cell count $n_o$ at a logarithmic growth phase $t_o$ becomes $n_1$ at $t_1$, $\mu$ is expressed by the following equation.

$$\mu = \frac{2.303 (\log n_1 - \log n_o)}{t_1 - t_o}$$

(11) After discarding bacteria having low $\mu$, the strains remaining are administered to various animals to judge practical use.

Properties of the bacteria according to the present invention are as follows.

I. Morphological properties of the representative bacteria according to present invention are shown in Table 3 below.

III. The physiological properties of the present microorganisms are shown in the following Table 5.

IV. Nutritional requirements of the bacteria deposited in Fermentation Research Institute are as follows, wherein a Stephenson-Wetham medium as a representative of inorganic salts and glucose was used as a basal medium; hereafter simply referred to as (S-W) medium.

TABLE 3

Morphology

| | IFO No. | | | | | |
|---|---|---|---|---|---|---|
| | 14253 | 14254 | 14255 | 14256 | 14257 | 14258 |
| Shape and Size of Cell | medium rod with round ends $0.7\mu \times 3\mu$ | short rod with round ends 1 to $3\mu$ | medium rod with round ends $0.8\mu \sim 4\mu$ | Same as the left | Same as the left | Same as the left |
| Polymorphism | negative | negative | negative | negative | negative | negative |
| Motility | — | — | — | — | — | — |
| Spore and Capsule | — | — | — | — | — | — |
| Gram-Staining | + | + | + | + | + | + |
| Acid Resistance | — | — | — | — | — | — |

(Note)
The morphology described above was a result when cultured on a bouillon medium but also when cultured on a bouillon-agar medium, the same morphology was shown (cultured at 37° C.).

II. Cultural characteristics of the representative bacteria in accordance with the present invention on various media are as shown in Table 4 below.

TABLE 4

Cultural Characteristics on Various Media

| | | IFO No. | | | | | |
|---|---|---|---|---|---|---|---|
| | | 14253 | 14254 | 14255 | 14256 | 14257 | 14258 |
| (1) | Bouillon-Agar Plate Culture | Colonies appeared about 15 hrs. after initiation of the culture. Circular 72 hrs. after; diameter 1.5 mm; elevation is capitate; smooth surface; wet; milky white; opaque gloss; no formation of diffusible pigment | Colonies appeared about 12 hrs. after initiation of the culture. Circular 72 hrs. after; diameter about 2 mm; elevation is high; smooth surface; wet; milky white; opaque gloss; no formation of diffusible pigment | Colonies appeared about 15 hrs. after initiation of the culture. Circular 72 hrs. after; diameter 1.5 mm; elevation is capitate; smooth surface; wet; milky white; opaque gloss; no formation of diffusible pigment | Same as the left | Same as the left | Same as the left |
| (2) | Bouillon-Agar Slant Culture | Grown thinly 12 hrs. after initiation of the culture; Color of the slant is milky white 72 hrs. after; glossy; elevation is moderate; no formation of diffusible pigment | Grown thinly about 10 hrs. after initiation of the culture; Color of the slant is milky white; glossy; elevation is high; no formation of diffusible pigment | Grown thinly 12 hrs. after initiation of the culture; Color of the slant is milky white 72 hrs. after; glossy; elevation is moderate; no formation of diffusible pigment | Same as the left | Same as the left (Cultured at 37° C.) | Same as the left |
| (3) | Bouillon Liquid Culture | Grown entirely but somewhat poor growth around the surface; opaque 72 hrs. after; Count $3.5 \times 10^9$/ml | Same as the left $5 \times 10^9$/ml | Same as the left $3.5 \times 10^9$/ml | Same as the left $3.5 \times 10^9$/ml | Same as the left $3 \times 10^9$/ml | Same as the left $3 \times 10^9$/ml |
| (4) | Bouillon-Gelatin Stab Culture | Grown at the stabbed portion alone; no gelatin liquefied | Same as the left | Same as the left | Same as the left | Same as the left | Same as the left |
| (5) | Litmus Milk | Formation of acid; coagulation of milk | Same as the left | Same as the left | Same as the left | Same as the left (Cultured at 37° C.) | Same as the left |

TABLE 5

| | IFO No. | | | | | |
|---|---|---|---|---|---|---|
| | 14253 | 14254 | 14255 | 14256 | 14257 | 14258 |
| Physiological Properties-(1) | | | | | | |
| Reduction of Nitrate | − | − | − | − | − | − |
| Denitrifying Reaction | − | − | − | − | − | − |
| MR Test | + | + | + | + | + | + |
| VP Test | − | − | − | − | − | − |
| Production of Indole | − | − | − | − | − | − |
| Production of Hydrogen Sulfide | − | − | − | − | − | − |
| Hydrolysis of Starch | − | − | − | − | − | − |
| Utilization of Citric Acid | − | − | − | − | − | − |
| Utilization of Inorganic Nitrogen Source | $NH_4^+$ is accessible in the presence of amino acid and vitamin. | Same as the left | $NH_4^+$ and $NO_3^-$ are not accessible. | Same as the left | $NH_4^+$ is accessible in the presence of amino acid. $NO_3^-$ is not accessible. | Same as the left |
| $NO_3^-$, $NH_4^-$ | $NO_3^-$ is not accessible. | | | | $NO_3^-$ is not accessible. | |
| Urease | − | − | − | − | − | − |
| Oxidase | − | − | − | − | − | − |
| Catalase | − | − | − | − | − | − |
| Behavior to Oxygen | Anaerobic or Slightly Anerobic | Same as the left | Same as the left | Same as the left | Same as the left | Same as the left |
| O-F Test | F | F | F | F | F | F |
| Production of Dye | − | − | − | − | − | − |
| Growth Range | | | | | | |
| Temperature | 18–45° C. | 15–45° C. | 18–45° C. | 18–45° C. | 16–45° C. | 16–45° C. |
| pH | 4–9 | 4–9.5 | 4–9 | 4–9 | 4–9 | 4–9 |
| Physiological Properties-(2) | | | | | | |
| L-Arabinose | − | − | − | − | − | − |
| D-Xylose | + | − | − | − | − | − |
| D-glucose | + | + | + | + | + | + |
| D-Mannose | + | + | − | − | + | + |
| D-Fructose | + | + | + | + | + | + |
| D-Galactose | − | + | + | + | + | + |
| Maltose | + | + | + | − | + | − |
| Sucrose | − | + | − | − | + | + |
| Lactose | + | + | + | + | + | + |
| Trehalose | − | + | + | + | + | + |
| D-Sorbitol | − | + | − | − | − | − |
| D-Mannitol | − | + | − | − | − | − |
| Inositol | − | − | − | − | − | − |
| Glucerin | − | + | − | − | − | − |
| Starch | + | + | − | − | − | − |

(note)
Results obtained by culture for 7 days (culture temperature at 37° C.)
No gas was formed in any case.

Experiments were performed, using ATCC 4357, 4962 and 9857 chosen for *L. acidophilus,* ATCC 8003 chosen for *L. brevis* and ATCC 12369 chosen for *L. fermentum,* as bacteria to be tested. It was made clear that when 500 mg of $Na_2S.9H_2O$ was poured onto a medium, these bacteria did not consume it.

In conclusion, the bacteria group of the present invention is markedly different from strains well known heretofore in that the members thereof have a capability of decreasing $Na_2S.9H_2O$ and $NH_3$ or, hydrogen sulfide, ammonium sulfide, methylmercaptan, ethylmercaptan, dimethyl sulfide, diethyl sulfide, acetaldehyde, skatol, methylamine, ethylamine, diethylamine, triethylamine (see Example 2), etc., but still possess all of the various properties of conventional Lactobacillus. At present, any difference other than described above cannot be recognized.

IV. Nutritional requirements of the bacteria deposited in Fermentation Research Institue are as follows, wherein a Stephenson-Wetham medium as a representative of inorganic salts and glucose was used as a basal medium; hereafter simply referred to as (S-W) medium.

TABLE 6

| | IFO. No. | | | | | |
|---|---|---|---|---|---|---|
| | 14253 | 14254 | 14255 | 14256 | 14257 | 14258 |
| (S-W) | − | − | − | − | − | − |
| (S-W) + Cystine | − | + | − | − | − | − |
| (S-W) + Cystine + $B_1$ | − | + | − | + | + | + |
| (S-W) + Cystine + C | − | + | − | − | + | + |
| (S-W) + Cystine ± Pantothenic Acid | − | + | − | + | + | + |
| (S-W) + Cystine + $B_1$ + C | + | + | + | + | + | + |
| (S-W) + Cystine + $B_1$ + Pantothenic Acid | + | + | + | + | + | + |
| (S-W) + Cystine + C + Pantothenic Acid | + | + | + | + | + | + |

TABLE 6-continued

| | IFO. No. | | | | | |
|---|---|---|---|---|---|---|
| | 14253 | 14254 | 14255 | 14256 | 14257 | 14258 |
| (S-W) + Vitamins | − | − | − | − | − | − |
| (S-W) + Casamino Acid | − | + | − | − | + | + |
| (S-W) + Vitamins + Casamino Acid | + | + | + | + | + | + |

+: grow
−: does not grow
The same results were obtained when cystine was replaced by other sulfur-containing amino acids.

From the results shown in Table 6, the following are understood.

It is found the IFO No. 14254 can grow only with inorganic materials+glucose+cystine. Further, IFO Nosx. 14256, 14257 and 14258 further requires the presence of vitamin $B_1$.

IFO No. 14253 and 14255 cannot grow with any one of vitamin $B_1$, vitamin C and pantothenic acid but can grow with the combination of two of them.

However, any of strains belonging to the *clearans* species cannot grow with (S-W)+vitamins but can grow with (S-W)+vitamins+casamino acids. This property of growth with these three nutrients is the same as those of Lactobacilli which are commercially available.

Lactobacilli which residue in the intestine and which are well known heretofore, are compared with the bacteria of the present invention, which comparison is set forth below.

Among Lactobacilli, acidophilus, brevis, fermentum and the like are said to be generally of enteric-habitat. It is extremely notable how these bacteria behave against $Na_2S.9H_2O$ and $NH_3$ since these two materials ($Na_2S.9H_2O$ and $NH_3$) are considered to be representative of enteric feculence.

Experiments were performed, using ATCC 4357, 4962 and 9857 chosen for *L. acidophilus*, ATCC 8003 chosen for *L. brevis* and ATCC 12369 chosen for *L. fermentum*, as bacteria to be tested. It was made clear that when 500 mg of $Na_2S.9H_2O$ was poured onto a medium, these bacteria did not consume it.

In conclusion, the bacteria group of the present invention is markedly different from strains well known heretofore in that the members thereof have a capability of decreasing $Na_2S.9H_2O$ and $NH_3$ or, hydrogen sulfide, ammonium sulfide, methylmercaptan, ethylmercaptan, dimethyl sulfide, diethyl sulfide, acetaldehyde, skatol, methylamine, ethylamine, diethylamine, triethylamine (see Example 2), etc., but still possess all of the various properties of conventional Lactobacillus. At present, any difference other than described above cannot be recognized.

The bacteria of the present invention may have a resistance to $Na_2S.9H_2O$ and/or $NH_3$. Culture to obtain resistance is carried out at 37° C. for 72 hours on 1 liter of medium (pH 6.0 to 7.0), as a basal medium, consisting of 10 g of meat extract, 10 g of peptone, 2 g of NaCl, 1 g of glucose, 1 g of $CaCO_3$ and 0.1 g of yeast extract, to which $Na_2S.9H_2O$ and/or $NH_3$ are added. Resistance of each of the bacteria to $Na_2S.9H_2O$ and $NH_3$ is thus examined. The preparation Example of the bacteria of the present invention will be described in the following.

PREPARATION EXAMPLE

Isolation of the bacteria group in accordance with the present invention is carried out as follows:

(1) Composition containing 5 g of meat extract, 5 g of peptone, 0.3 g of $Na_2S.9H_2O$, 3 g of sodium butyrate, 5 g of glucose and 3 g of $CaCO_3$ was prepared. The pH was modified to neutral and diluted feces of mankind was coated on the medium followed by anaerobic culturing at 37° C.

(2) Among appeared colonies, colonies having a transparent margin were fished.

(3) The colonies were spread over an LBS medium followed by culturing at 37° C. for 2 days.

(4) Grown colonies were fished and stab culture was carried out on a butt medium consisting of 10 g of meat extact, 10 g of peptone, 2 g of NaCl, 10 g of glucose, 5 g of lime and 10 g of agar to collect gas-non-producing bacteria.

(5) Various tests were performed to see if the properties of the bacteria were consistent with those of Lactobacilli and it was confirmed that the bacteria was classified and Lactobacilli from a taxonomy standpoint.

(6) Hemolytic test was carried out to collect non-hemolytic bacteria.

Thus, *Lactobaccilus sulfurica*, IFO 14255 was obtained.

Hereafter usefulness of the bacteria of the present invention will be described with reference to the following example.

EXAMPLE 1

In case that the bacteria of the present invention is incorporated in cream which is inherently liable to undergo putrefaction, or further followed by fermentation and enrichment, the extension of the time period of putrefaction and relation to the bacterial count formed were examined.

Cream used in the experiments and the composition are as follows:

(a) castered cream: 75 g of wheat flour, 125 g of sugar, 500 ml of milk, 4 yolks and 5 g of salt-free butter were heated with stirring (b) whipped cream: 1 bottle of fresh cream and 10 g of sugar Bacteria and Differential Name:

*Lactobacillus acidophilus, Lactobacillus brevis, Lactobacillus fermentum*, etc. which are well known heretofore are collectively termed HW Group hereafter; Lactobacillus bacteria sufficiently finished so as to be suited for mass production, which are commercially available, termed C group, and the bacteria group *L. clearans* of the present invention termed TI Group.

EXPERIMENT (A)

Results obtained when Lactobacillus of each of the groups was inoculated and grown on cream.

Bacteria belonging to the aforesaid HW group, C group and TI group were injected into aseptic castered cream at 50,000,000 cell counts/g, respectively. The degree of the growth of the bacteria measured 38, 72 and 96 hours after inoculation when allowed to stand at 37° C. is shown in FIG. 1 in the form of a graph.

As is clear from the graph shown in FIG. 1, it is well noted that the growth of the bacterial count is extremely larger in the TI group than the other groups. This depends on the strain but there are many strains exceeding $10^9$ cell count 72 hours after culturing. The numerical figure "50,000,000 cell counts" as the amount of bacteria added was obtained as a result of investigating the optimum addition amount in preparation. In the practice of the present invention, however, one is not always restricted to this figure.

EXPERIMENT (B)

Bacterial count when various bacteria contaminate cream and grow.

It is heretofore known that *E. coli*, Staphylococcus and *B. subtilis* can be regarded as representatives of potent bacteria among general bacteria and putrefactive bacteria. Accordingly, progress of putrefaction and thus storability of cream were studied by examining the growth of these three in cream.

Staphylococcus 209P, *E. coli* ATCC 25922 and *B. subtilis* ATCC 6633 were incorporated in castered cream at 5, 10,000 and 50,000,000 cell counts/g, respectively and allowed to grow to examine the manner of the growth.

Figure 2:
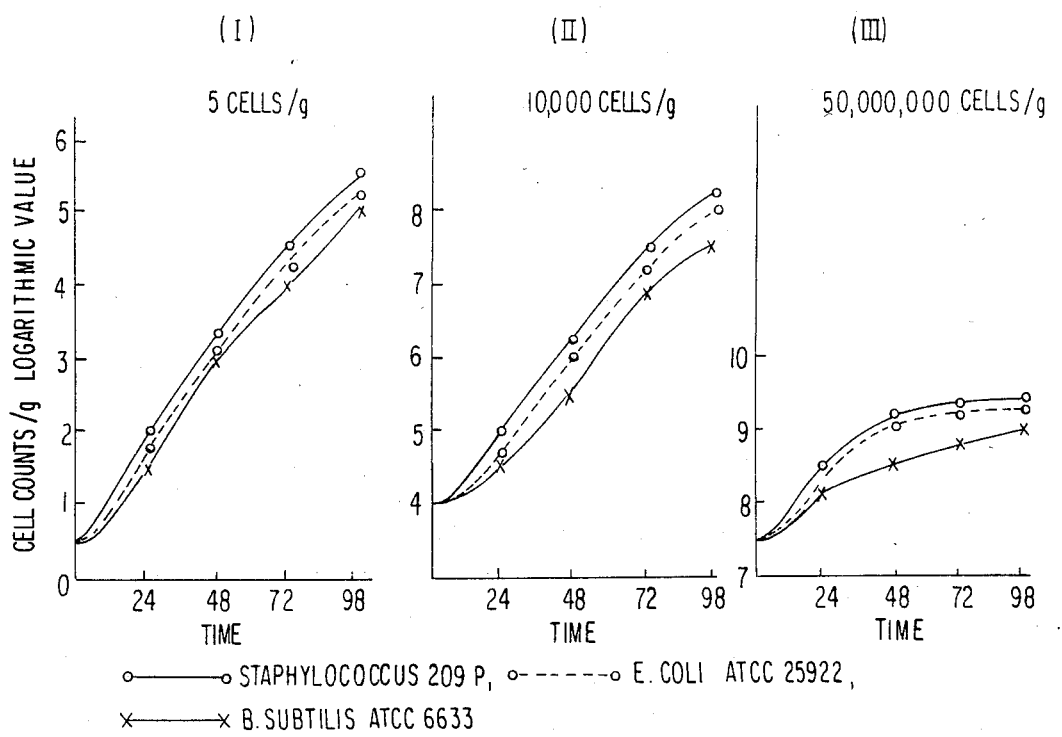
FIGS. 2 (I), (II) and (III) are graphs showing growth curves for Staphylococcus, *E. coli* and *B. subtilis* in cream.

The results are shown in FIGS. 2 (I), (II) and (III).

As is also clear from the graphs in FIGS. 2, Staphylococcus is most potent in growth and the growth of this strain is noted to a destructive extent in the infections of 10,000 cell counts and further 50,000,000 cell counts and, the data indicates that it is dangerous for whipped cream to be stored for more than 1 day.

EXPERIMENT (C)

Bacterial count obtained when various bacteria and the bacteria of the present invention were inoculated and grown on aseptic cream, respectively.

Increase and decrease of each of the bacteria, i.e., interference, was examined in cases that (a) the production of cream was initiated, (b) growth was on the way, and (c) various bacteria were artificially mingled after the preparation, respectively and examined to determine which is best as a food.

The experiment was carried out in the cases of 50,000,000 cell counts as the addition amount of Lactobacillus; 5, 10,000 and 50,000,000 cell counts as the addition amounts of various bacteria as in Experiment (B). It appears that the indication of all the results would merely invite confusion and some results would be unnecessary in view of the progress of food production technology nowadays. Accordingly, representative data out of the entire data are given below and the other can be presented, if necessary.

(a) Experiment Relating to *E. coli*

(i) When Lactobacillus and *E. coli* are added to cream at the same time followed by fermentation at 37° C.

(1) Influence of Various Bacteria on the Lactobacillus of the Present Invention:

In the case of 5 cells of *E. coli*/g:

None of Lactobacilli belonging to the HW, C and TI groups was affected in growth. In the case of the addition at 10,000 cells/g:

The Lactobacilli belonging to the HW and C groups showed a bacterial count reduced by 10 to 30%, whereas the TI group was not affected.

(2) Influence of Lactobacillus on *E. coli*:

In the case of 5 cells of *E. coli*/g, it has been made clear that the grown cell count decreases to $\frac{1}{2}$ to $\frac{1}{3}$ by the HW group, $\frac{1}{4}$ to 1/20 by the C group and 1/40 to 1/300 (varies depending upon bacteria) by the TI group, as compared to the case where no Lactobacillus is present.

In the case of 10,000 cells of *E. coli*, the grown bacterial counts were generally doubled as compared to the cases of 5 cells; that is, no change in the HW group; $\frac{1}{2}$ to 1/10 by the C group and 1/20 to 1/150 by the TI group.

(ii) When *E. coli* was added 48 hours after the addition of Lactobacillus and initiation of fermentation:

(1) Influence of *E. coli* on Lactobacillus:

It was made clear that *E. coli* hardly affected the growth of the Lactobacillus in any cases of adding 5 cells and 10,000 cells.

(2) Influence on *E. coli*:

In the case that 5 cells were added, the bacterial count showed $\frac{1}{2}$ to 1/20 that of the case where the addition was simultaneous. Particularly where the bacteria belonging to the TI group was previously cultured, the bacterial count was slightly $1 \times 10^2$ or less. Also where 10,000 cells were added, the bacterial count was about $\frac{1}{2}$ to about 1/10 that of the simultaneous addition.

(iii) When *E. coli* was added after completion of lactic acid fermentation:

(1) Influence Lactobacillus undergoes:

It has been made clear that no Lactobacillus of any group was substantially affected.

(2) Influence *E. coli* undergoes:

It has been made clear that in the case of the bacteria belonging to the HW group and the C group, the bacterial count was almost the same as the case (ii)-(2). In the TI group, however, no growth was noted with the addition of 5 cells; even in the case of 10,000 cells, the bacterial count was merely $1 \times 10^5$ to $2 \times 10^5$, i.e., growth was merely about 10 to about 20 times.

(b) Experiment Relating to the Relationship between *B. subtilis* and Staphylococcus According to experiment similar to that using *E. coli* described above, in the case of *B. subtilis*, the bacterial count of *B. subtilis* becomes about 50% the case of *E. coli*, due to interference undergone by the growth of Lactobacillus. In the case of Staphylococcus, it was about 140% of the case of *E. coli*.

TABLE 9

| | | Item Tested | | |
|---|---|---|---|---|
| IFO No. | Bacterial Count in 1 g Yogurt | Period Given (6 days a week 12 times in total) | Response of Living Body during Period Given | Amount of Bacteria Excreted during Period Given (daily excretion is made 300 g) |
| 14253 | 2,000,000,000 | 4 months | good movement relieved fatigued | 150,000,000,000 cells |
| 14254 | 3,000,000,000 | " | good movement relieved | 250,000,000,000 cells |

TABLE 9-continued

| IFO No. | Bacterial Count in 1 g Yogurt | Period Given (6 days a week 12 times in total) | Response of Living Body during Period Given | Amount of Bacteria Excreted during Period Given (daily excretion is made 300 g) |
|---|---|---|---|---|
| 14255 | 2,000,000,000 | " | fatigued good movement relieved fatigued | 150,000,000,000 cells |
| 14256 | " | " | good movement relieved fatigued | " |
| 14257 | " | " | good movement relieved fatigued | 155,000,000,000 cells |
| 14258 | " | " | good movement relieved fatigued | 150,000,000,000 cells |

As is clear from the foregoing experimental results, the growth of various bacteria is strongly prevented by the addition and growth of the TI group bacteria of the present invention and it is possible to extend a time period for storage. In particular, it is becoming possible to extremely reduce the invasion of various bacteria, by the progress of production techniques these days. Accordingly, the known techniques can greatly contribute to prevention of cream spoiling in combination with the addition of the TI group bacteria.

Further concerning types of cream, the grown bacterial count in the case of whipped cream was approximately 70% of the case of castered cream.

EXAMPLE 2

A raw material consisting of 10 g of skim milk, 10 g of sugar, 0.2 g of agar and 100 ml of water was sterilized and the bacteria in accordance with the present invention were aseptically added thereto followed by fermentation for 24 hours. The thus prepared yogurt was administered to human twice a day (morning and evening) at about 400,000,000,000 cells in total and the relation between the bacteria and the human body was examined.

The results are shown in Tables 9 and 10.

Yogurt obtained from one strain was administered to 5 adult volunteers, respectively, but none showed extremely different results from the others and thus the totalized results are summarized in the tables.

As is also shown in the table above, no adverse effect was noted with the living body even when the four strains of L. clearans, two strains of L. sulfurica and two strains of L. nitrosus were all administered in large amounts over long periods of time. Administration of two strains selected from L. sulfurica and L. nitrosus produces the same effects as those shown in the above Table 9. Not only that, all of the volunteers noted the conditions that fatigue was relieved and better movements were obtained on about the 3rd day after the initiation of the yogurt.

TABLE 10

| IFO No. | Purification of Enteric Putrid Material Amount Reduced (%)* | Retention Time of Bacteria Administered | Influence on Enteric Bacterial during Administration of Bacteria |
|---|---|---|---|
| 14253 | 10% | 2 to 3 days | Slight variation of cell count. No omission of bacteria |
| 14254 | 20% | 3 to 6 days | Slight variation of cell count. No omission of bacteria |
| 14255 | 10% | 2 to 3 days | Slight variation of cell count. No omission of bacteria |
| 14256 | 11% | " | Slight variation of cell count. No omission of bacteria |
| 14257 | 12% | " | Slight variation of cell count. No omission of bacteria |
| 14258 | 10% | " | Slight variation of cell count. No omission of bacteria |

*The measurement method was in accordance with a extinction method, a gas chromatography method (GC analysis method), a GC-orfactometer method (GC-OM method), GC-mass spectrometer method (GC-MS analysis method), etc. Substances to be measured were hydrogen sulfide, ammonia, methylmercaptan, ethylmercaptan, dimethyl sulfide, acetaldehyde, skatol, propionic acid, butyric acid, and trimethylamine. The reduced amount of the substances measured is expressed by the percent figure.

The retention time is expressed as a time period required for the amount of the bacteria excreted being reduced to 1/10 of the amount of the bacteria given. Also in this case, the fetal excretion amount was made 300 g a day. For example, in the 6587 bacteria, the number of days from 150,000,000,000 cells excretion daily due to administration of 400,000,000,000 cells daily to the excretion being decreased to less than 40,000,000,000 after the discontinuation of the administration was from 2 to 3 days with the 5 volunteers.

The reduced amount (%) of the Table 10 is the arithmetic mean of the reduced amounts of each bad-smelling substances. The L. sulfurica reduces the amount of bad-smelling S-compound, the L. Nitrosus the amount of bad-smelling N-compound, and the clearans the amount of both bad-smelling compounds.

The reduced amounts (%) in Table 10 are results of analysis in excrement 7 days after a beginning of administration. Continuous administration, for example for 20 days, leads to better result than that of the Table 10 by about twice.

Further, it is confirmed that amounts of microorganisms in yogult increases to produce a further effect by extension of fermentation period to 35–48 hours.

*L. sulfurica* and *L. nitrosus* have activities only to reduce amounts of S-compounds and N-compounds, respectively. The combination thereof, however, has the same activity as that of *L. clearans*. Therefore, the combination thereof may be useful for Lactobacillus preparation, Lactobacillus drinks, etc., instead of *L. clearans*.

With respect to enteric bacteria the normal enteric bacterial floras of 8 bacterial types, including Lactobacillus, inherently possessed by the volunteers, were traced one by one. As shown in Table 10, the results indicate that no species were omitted and slight change was noted either during the administration or after the discontinuation of the administration.

With respect to Lactobacillus, possible best efforts have been made to prove that Lactobacillus is non-toxic and non-pathogenic. In these days, however, it has been made clear that it is necessary and indispensable for maintaining health that more than certain amounts of Lactobacilli inhabit the living body, in particular, the mucous membrane. In light of such a finding, it is understood that according to the present invention, injection of bacteria having strong autogrowth power and strong exclusion power such as the bacteria of the present invention into edible cream (as a very easily putrified material) and further allowing them to grow there are not only useful for extending the time period of putrefaction of cream but are also effective for reducing putrid substances in the intestine and regulating the intestinal movements, etc.

Antibiotics which are being developed recently have extremely potent effects and wide antibacterial spectrum; accordingly, these antibiotics often cause considerable disturbance of enteric bacterioflora, when administered to the human body. When the bacteria of the present invention is administered at large doses in such a case, it assists to repair bacterioflora after the discontinulation of drug administration and recovery of health. The present invention has an extremely significant utility from an industrial view point.

As the present bacteria are surely Lactobacillus, those have properties which well known Lactobacillus carries, and thus have a strong affinity to mucous membrane. Further, activity and a characteristic of nutrient requirement and $\mu$-value are enormous and, thus, fixing ability to the mucous membrane etc. is much larger than that of other well known Lactobacillus bacteria. Therefore, the present bacteria are useful for intestine, orad cavity, vagina suppository etc. The present invention has an extremely significant utility, especially sanitary industry.

The bacteria of the present invention is characterized by that the bacteria of the present invention reduces the amounts of bad-smelling S-compounds and/or N-compounds, while well known bacteria, such as *Lactobacillus acidophilus* cause ni influence on these compounds and that the bacteria of the present invention only reduces the amounts of bad-smelling compounds, while bacteria previously patented (*Lactobacillus deodorans*) in Japanese Pat. No. 49193/82 and UK Pat. No. 1,584,694 reduce completely them to a degree that the remained bad-smelling compounds are not measured. This is exerted by the property that *Lactobacillus deodorans* assimilates bad-smelling compound in preference to glucose, i.e., assimilating whole bad-smelling compounds and, while, the present bacteria, such as *Lactobacillus clearans* does not assimilate bad-smelling compound completely to leave bad-smelling compounds without assimilation.

The present bacteria is discriminated from *Lactobacillus deodorans* in view of that, in the former, larger amounts or long period of administration, or abrupt suspension of administration causes no disturbance on intestine bacteria in the living body and, while, in the latter, those administration sometimes cause disturbance on intestine bacteria.

While the invention has been described in detail and with reference to specific embodiments thereof, it will be apparent to one skilled in the art that various changes and modifications can be made therein without departing from the spirit and scope thereof.

What is claimed is:

1. A substantially pure culture of *Lactobacillus clearans*, *Lactobacillus sulfurica* or *Lactobacillus nitrosus*:
    (A) which can metabolize both $Na_2S.9H_2O$ and/or $NH_3$ when inoculated and cultured on:
        a medium comprising 5 g of meat extract, 5 g of peptone, 0.5 g of $Na_2S.9H_2O$, 5 g of glucose, 1 g of $CaCO_3$, 0.5 ml of $NH_3$ (as 100% ammonia) and 1 liter of water (pH, neutral);
    (B) which shows no growth acceleration action even when said bacteria is cultured on a medium comprising a Stephenson-Wetham medium; $KH_2PO_4$ 1 g, $MgSO_4.7H_2O$ 0.7 g, NaCl 1 g, $(NH_4)_2HPO_4$ 4 g; $FeSO_4.7H_2O$ 0.03 g, glucose 5 g)+vitamins (A: 900 IU, $B_1$: 1 mg, $B_2$: 1 mg, $B_6$: 1 mg, $B_{12}$: 5 gamma, nicotinamide: 1.6 mg, calcium pantothenate: 8 mg, C: 64 mg, $D_2$: 120 IU)+casamino acid 1 g and where 0.5 g of $Na_2S.9H_2O$ and/or 0.5 ml (100% conversion) of $NH_3$ are incorporated at the logarithmic growth phase; and;
    (C) which has the following characteristics;
        gram-positive, rod, non-motile, catalase-negative, no reduction of nitrates, no decomposition of gelatin, no formation of indole or hydrogen sulfide, high ability of forming lactic acid from glucose and lactose, and growth being accelerated by the addition of acetic acid.

2. The substantially pure culture of the Lactobacillus of claim 1 selected from the group consisting of IFO 14253, 14254, 14255, 14256, 14257 and 14258.

3. An edible food comprising a food and the Lactobacillus of claim 1 in an amount sufficient to effect the intestinal bacterial flora and/or amounts of noxious substances in the intestine.

4. An edible food comprising a food and the Lactobacillus of claim 2 in an amount sufficient to effect the intestinal bacterial flora and/or amounts of noxious substances in the intestine.

5. A process for regulating the intestinal bacterial flora or noxious substances in the intestine which comprises orally administering an effective amount of the Lactobacillus of claim 1.

6. A process for regulating the intestinal bacterial flora or noxious substances in the intestine which comprises orally administering an effective amount of the Lactobacillus of claim 2.

7. A method for delaying putrefaction of a food substance which comprises inocultating said food substance with the Lactobacillus of claim 1.

8. A method for delaying putrefaction of a food substance which comprises inoculating said food substance with the Lactobacillus of claim 2.

9. An edible food as claimed in claim 3, wherein said noxious substances are selected from the group consisting of $NH_3$, $H_2S$, butyric acid, compounds containing sulfur atoms, nitrogen atoms and carbon atoms found in the intestine and mixtures thereof.

10. An edible food as claimed in claim 4, wherein said noxious substances are selected from the group consisting of $NH_3$, $H_2S$, butyric acid, compounds containing sulfur atoms, nitrogen atoms and carbon atoms found in the intestine and mixtures thereof.

11. An edible food as claimed in claim 5, wherein said noxious substances are selected from the group consisting of $NH_3$, $H_2S$, butyric acid, compounds containing sulfur atoms, nitrogen atoms and carbon atoms found in the intestine and mixtures thereof.

12. An edible food as claimed in claim 6, wherein said noxious substances are selected from the group consisting of $NH_3$, $H_2S$, butyric acid, compounds containing sulfur atoms, nitrogen atoms and carbon atoms found in the intestine and mixtures thereof.

* * * * *